United States Patent
Horn et al.

(10) Patent No.: US 8,431,410 B2
(45) Date of Patent: Apr. 30, 2013

(54) AMINE-N-OXIDE REDOX INDICATORS FOR FLUORIMETRIC DETERMINATION OF ANALYTES

(75) Inventors: Carina Horn, Alsbach-Haehnlein (DE); Joachim Hoenes, Zwingenberg (DE); Jürgen Spinke, Lorsch (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 434 days.

(21) Appl. No.: 12/757,372

(22) Filed: Apr. 9, 2010

(65) Prior Publication Data

US 2010/0221699 A1  Sep. 2, 2010

Related U.S. Application Data

(62) Division of application No. 10/771,872, filed on Feb. 4, 2004, now Pat. No. 7,723,121.

(51) Int. Cl.
    *G01N 21/76* (2006.01)
(52) U.S. Cl.
    USPC ............ 436/172; 436/800; 436/904; 436/14; 436/16; 435/25; 435/7.9
(58) Field of Classification Search ............... None
    See application file for complete search history.

(56) References Cited

U.S. PATENT DOCUMENTS

| | | | |
|---|---|---|---|
| 4,358,595 A | 11/1982 | Ghosh et al. |
| 5,334,508 A | 8/1994 | Hoenes |
| 6,312,906 B1 | 11/2001 | Cass et al. |
| 6,872,573 B2 | 3/2005 | Albarella et al. |
| 7,378,255 B2 | 5/2008 | Horn et al. |
| 2002/0160400 A1 | 10/2002 | Lakowicz |

FOREIGN PATENT DOCUMENTS

DE   198 00 537 A1   10/1998

OTHER PUBLICATIONS

Thompson, S. et al. Mutagenicity of anti-cancer nitrobenzofuroxans, 1977, Mutation Research, vol. 48, pp. 145-154.*

(Continued)

*Primary Examiner* — Robert Xu
(74) *Attorney, Agent, or Firm* — Dinsmore & Shohl, LLP

(57) ABSTRACT

A reagent for detecting an analyte by a redox reaction and a fluorimetric determination is disclosed. The reagent comprises a compound of formula (I):

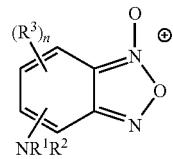

wherein $R^1$ and $R^2$ are each independently selected from R, $(CH_2CH_2O)_mR$, COR, COOR, and OCOR; each $R^3$ is independently selected from $NO_2$, CN, R, OR, OCOR, COOR, SR, and halogen; R is H or $C_1$-$C_4$ alkyl, where alkyl is optionally substituted with one or more functional group independently selected from the group consisting of halogen, OR, SR, $NR_2$, COOR, $CONR_2$, $SO_3R$ and salts thereof, and $PO(OR)_3$ and salts thereof; m is an integer from 1 to 20; and n is 1, 2, or 3. The reagent may further comprise an enzyme or a coenzyme for reducing or oxidizing an analyte.

15 Claims, 1 Drawing Sheet

OTHER PUBLICATIONS

Longmuir, K., Martin, O., Pagano, R. "Synthesis of Fluorescent and Radiolabeled Analogues of Phosphatidic Acid", Chemistry and Physics of Lipids, 36 (1985) 197-207, Elsevier Scientific Publishers Ireland Ltd.

Rasmussen, S., Carroll, F., Maresch, M., Jensen, A., Tate, C., Gether, U., "Biophysical Characterization of the Cocaine Binding Pocket in the Serotonin Transporter Using a Fluorescent Cocaine Analogue as a Molecular Reporter", The Journal of Biological Chemistry, 2001, vol. 276, No. 7, Feb. 16, pp. 4717-4723.

Viguier, M., Dornmair, K., Clark, B., McConnell, H., "The invariant chain forms complexes with class II major histocompatibility complex molecules and antigenic peptides in vivo", Proc. Natl. Acad. Sci. USA, vol. 87, pp. 71 70-71 74, Sep. 1990.

"Chemdraw" of 7-Nitro-benz-2,1,3-oxadiazol.

Ghosh, P.B. et at, Journal of Medicinal Chemistry (1968) pp. 305-311.

Shipton, M., Stuchbury, T., Brocklehurst, K., "Evaluation of Benzofuroxan as a Chromophoric Oxidizing Agent for Thiol Groups by using its Reactions with Papain, Ficin, Bromelain and Low-Molecular-Weight Thiols", Biochem J. (1 977) 161,627-637 (printed in Great Britain).

Database WP1, Section Ch, Week 198 1 18, Derwent Publications Ltd., London, GB; AN 198 1-321 60d, XP002283234 & SU 757 943 A (Druzhinin A A), Aug. 25, 1980.

Database WP 1, Section Ch, Week 199541, Derwent Publications Ltd., London, GB; p. 3, AN 1995-035059, WOO2283235 & RU 2 012 869 C (Univ. Kazan Techn).

Database WP1, Section Ch, Week 199345, Derwent Publications Ltd., London, GB; p. 3, AN 1993-358217, XP 002283236.

Wang et al., "The Influence of High-Temperature Water on the Reaction Pathways of Nitroanilines", The Journal of Supercritical Fluids, 1995, 8, pp. 236-249.

\* cited by examiner

AMINE-N-OXIDE REDOX INDICATORS FOR FLUORIMETRIC DETERMINATION OF ANALYTES

CROSS-REFERENCE TO RELATED APPLICATIONS

The present application is a divisional of U.S. patent application Ser. No. 10/771,872, filed Feb. 4, 2004, now U.S. Pat. No. 7,723,121. The present application claims priority under 35 U.S.C. §119 to German Application No. 103 04448.5 filed Feb. 4, 2003.

BACKGROUND

The invention concerns methods and reagent kits for the fluorimetric determination of analytes.

There are numerous methods for determining analytes for example for diagnostic applications. One method is to determine the analyte by means of a redox reaction and a redox indicator. In this case an oxidizing or reducing system acts directly on the redox indicator or via a mediator. The presence of the analyte leads to a reduction or oxidation of the redox indicator which enables a qualitative or quantitative determination to be carried out.

Depending on the type of redox indicator that is used, the indicator can be determined by a colorimetric, fluorimetric or electrochemical detection method. Examples of colorimetric detection reagents are heteropolyacids (EP-B-0 431 456), tetrazolium compounds (EP-B-0 574 769), nitrosoaromatic compounds (EP-A-0 620 283), RIND compounds (EP-B-0 190 740), phenazines (WO 93/06487) and indanthrones (EP-B-0 831 327). Examples of electrochemical detection reagents are nitrosoaromatics, phenazines, potassium hexacyanoferrate and benzoquinones (cf. e.g. EP-A-0 441 222 and EP-A-0 505 494). Examples of fluorimetric detection reagents are e.g. resazurin (U.S. Pat. No. 5,912,139), transition metal complexes (Ryabov et al., JBIC 4 (1999) 175-182; Woltman et al., Anal. Chem. 71 (1999) 1504-1512) and scopoletin, esculetin, p-hydroxyphenylacetic acid, di-chlorofluorescein, N-acetyl-3,7-dihydroxyphenoxazine and MNBDH which are used exclusively for the detection of $H_2O_2$ (see also R. Haughland, Handbook of Fluorescent Probes and Research Chemicals, $6^{th}$ edition 1996).

However, the fluorimetric detection reagents known from the prior art have some disadvantages. Thus most known fluorescent indicators require that metabolites such as glucose are determined by detecting $H_2O_2$ generated by glucose oxidase. This reaction usually has to be catalytically supported by the enzyme peroxidase and is very prone to interference by electron donors such as urea or bilirubin. The reagents are also not stable for long time periods.

In contrast, redox indicators that allow an oxygen-independent detection of glucose i.e. which directly accept an electron from an oxidizing enzyme instead of oxygen, are advantageous. However, only resazurin and Os and Ru complexes are known to be suitable electron acceptors for this. However, in the case of resazurin the emission bands of the resorufin formed by the redox reaction strongly overlap the absorption bands of non-reacted resazurin which considerably reduces the sensitivity of the analyte determination. The high redox potential of transition metal complexes (e.g. Ru complexes) results in a strong interference by compounds such as ascorbic acid. Their fluorescence efficiency also varies with the oxygen content of the sample.

Furthermore in the case of the previously known fluorescent indicators the excitation light sources used are mainly limited to the UV and green range of light. Thus for example an inadequate number of compounds are known which allow use of the particularly strong blue and red LEDs.

SUMMARY

Hence one object of the present invention was to provide new redox-active compounds as detection reagents for the fluorimetric determination of analytes which enable the disadvantages of the prior art to be at least partially eliminated.

This object is achieved according to the invention by providing the N-oxide of NBD-amine or derivatives thereof as redox indicators. NBD is the abbreviated form of "7-nitrobenzo-2-oxa-1,3-diazol." The NBD-amine formed by reduction is characterized by a high fluorescence and can be very readily excited with blue light radiation.

Hence a first aspect of the present invention is a method for detecting an analyte by a redox reaction and a fluorimetric determination characterized in that a sample containing the analyte is contacted with a detection reagent which contains a compound of the general formula (I) as a fluorimetric redox indicator:

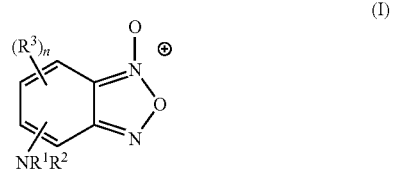

(I)

in which $R^1$ and $R^2$ are each independently selected from R, $(CH_2CH_2O)_mR$, COR, COOR and OCOR,
$R^3$ in each case is independently selected from $NO_2$, CN, R, OR, OCOR, COOR, SR and halogen,
R is H or $C_1$-$C_4$ alkyl, where alkyl is optionally substituted with halogen, OR, SR, $NR_2$, COOR, $CONR_2$, $SO_3R$ and salts thereof or/and $PO(OR)_3$ and salts thereof, m is an integer from 1-20, preferably from 1-10 and n is 1,2 or 3.

Another aspect of the invention is a reagent for detecting an analyte by a redox reaction and a fluorimetric determination which contains a compound of the general formula (I) as described above as the fluorimetric redox indicator.

The present invention is suitable for detecting any analytes that can be determined by a redox reaction. The detection can be qualitative, semi-quantitative or quantitative. In one embodiment of the invention the analyte can be a reducible or oxidizable substance, for example a metabolite present in a body fluid such as blood, serum, plasma, urine etc. In this case it is expedient to use a detection reagent which, in addition to the redox indicator, also contains one or more enzymes for reducing or oxidizing the analyte and optionally coenzymes such as nicotine nucleoside derivatives e.g. $NAD^+$, $NADP^+$ or flavin nucleoside derivatives e.g. FAD. Preferred examples of such analytes are glucose, lactate, alcohol, galactose, cholesterol, fructose, glycerol, pyruvate, creatinine, alanine, phenylalanine, leucine, triglycerides, HDL-cholesterol. Glucose can for example be detected by known methods using glucose oxidase (GOD), glucose dye oxidoreductase (GlucDOR) or glucose dehydrogenase (GDH)/diaphorase.

Furthermore the analyte may also be an enzyme that catalyses a redox reaction, for example an oxidoreductase such as glucose oxidase, glucose dye oxidoreductase, dehydrogenases or an enzyme whose reaction can be coupled to an oxidoreductase reaction.

In addition to the redox indicator and, if required, an enzyme for reducing or oxidizing the analyte, the detection reagent can additionally contain common components such as coenzymes, auxiliary substances, buffers and optionally mediators. Substances are suitable as mediators which support the acceptance of electrons by the redox indicator (I). However, in general those redox indicators are preferred which can directly accept electrons.

The method according to the invention is carried out in conventional test formats such as in dry or wet tests. In a dry test an absorbent material, e.g. in the form of a test strip, is used as a support on which the detection reagent can be applied in a dry form e.g. as a lyophilisate. Liquid tests are carried out in a liquid phase in suitable reaction vessels e.g. cuvettes, microtitre plates etc. where the detection reagent can be provided in the reaction vessel itself or in separate containers in a dry or liquid form.

For a fluorimetric determination, the sample is irradiated with excitation light of a predetermined wavelength and the fluorescence emission light emitted by the sample that has a different wavelength is determined by known methods. Suitable variation of the substituents $R^1$, $R^2$ and $R^3$ enables the present invention to provide optimized test formats for the determination of any analytes.

It is preferable that the redox indicator (I) has one or more hydrophilic groups, e.g. OR groups, COOR groups etc., to increase solubility. In a particularly preferred embodiment $R^1$ and $R^2$ are $C_{1-2}$ alkyl groups substituted with OR such as hydroxyethyl groups or polyoxyethylene groups. $R^3$ is preferably $NO_2$ and n is 1. A particularly preferred example of a redox indicator according to the invention is shown in FIG. 1.

Another aspect of the invention is a reagent for detecting an analyte by a redox reaction and a fluorimetric determination comprising a compound of the general formula (I) as stated above as the redox indicator.

In addition to the redox indicator, the reagent according to the invention can also contain other components selected from enzymes, coenzymes, auxiliary substances, buffers and mediators.

The present invention is further elucidated by the following figures and the example.

DETAILED DESCRIPTION

EXAMPLE

Glucose determination using an NBD-amine-N-oxide as the redox indicator.

The following compounds were added to a 3 ml fluorescence cuvette (the stated concentrations refer to the final concentration in the cuvette; the N-oxide of the NBD-amine was prepared according to P. B. Ghosh, M. W. Whitehouse, J. Med. Chem., 11, 305-311 (1968)):

| | |
|---|---|
| glucose dehydrogenase (GlucDH): | 1.3 U/ml |
| diaphorase: | 1.3 U/ml |
| NAD⁺: | 36.9 µmol/l |
| N-oxide of the NBD-amine: | 35.4 µmol/l |

The reaction was started by adding an aqueous glucose solution (0.1 M phosphate buffer, pH 7.4 containing 1% NaCl). The kinetics of the reaction were recorded for various glucose concentrations at an excitation wavelength of 470 nm and an emission wavelength of 560 nm. The result of the experiment is shown in FIG. 2.

Figure 1:
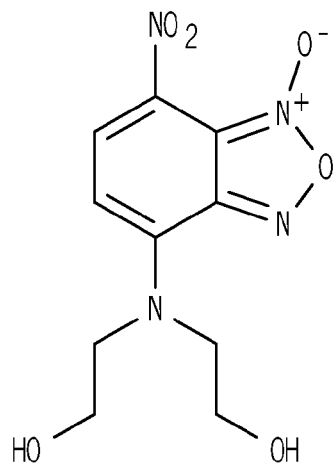
FIG. 1 shows the N-oxide of the NBD-amine as an example of a redox indicator according to the invention.
Figure 2:
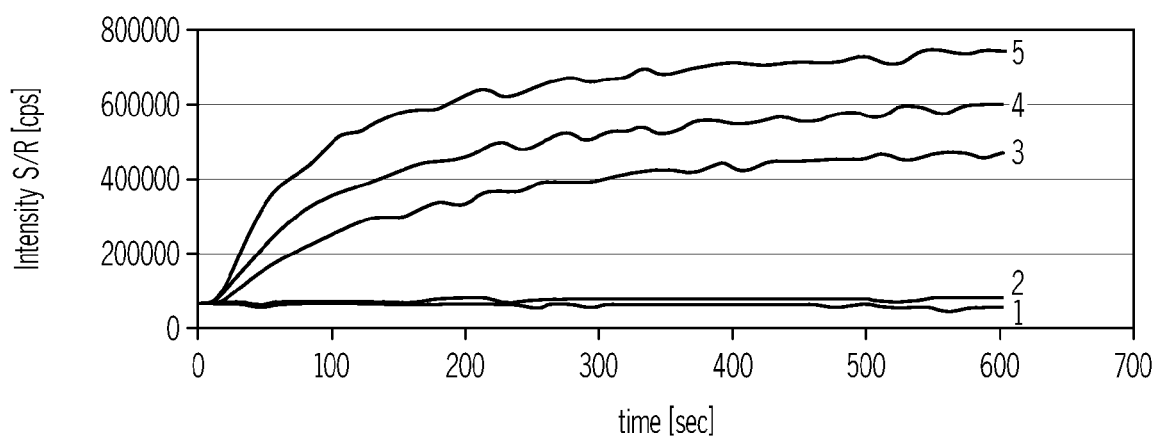
FIG. 2 shows the kinetics of the NBD-amine-N-oxide reduction in a system for detecting glucose at various glucose concentrations.

FIG. 2, in which the intensity of the fluorescence signal (intensity) in impulses per second (cps) is plotted versus time in seconds (sec), shows that an increase in fluorescence is found which is proportional to the glucose concentration present in the sample. In this case the measuring curves 1 to 5 correspond to glucose concentrations of 0, 0.06, 1.2, 2.4 and 4 (each in mg/dl).

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A reagent kit that detects a reducible or oxidizable analyte by a redox reaction and a fluorimetric determination, the reagent kit comprising:
   (a) one or more enzymes that reduce or oxidize the reducible or oxidizable analyte; and
   (b) a redox indicator that is oxidized or reduced in the presence of both
      (i) the reducible or oxidizable analyte, and
      (ii) the one or more enzymes
   by accepting an electron, directly or via a mediator, from the reducible or oxidizable analyte, the redox indicator being a compound of formula (I):

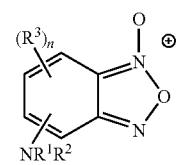

(I)

wherein
   $R^1$ and $R^2$ are each independently selected from R, $(CH_2CH_2O)_m R$, COR, COOR, and OCOR;
   each $R^3$ is independently selected from $NO_2$, CN, R, OR, OCOR, COOR, SR, and halogen;
   R is H or $C_1$-$C_4$ alkyl, where alkyl is optionally substituted with one or more functional group independently selected from the group consisting of halogen, OR, SR, $NR_2$, COOR, $CONR_2$, $SO_3R$ and salts thereof, and $PO(OR)_3$ and salts thereof;

m is an integer from 1 to 20; and n is 1, 2, or 3 wherein the reducible or oxidzable analyte is glucose and the one or more enzymes is selected from the group consisting of glucose oxidase, glucose dye oxidoreductase, and glucose dehydrogenase/diaphorase.

2. The reagent kit of claim 1, further comprising components selected from coenzymes, auxiliary substances, buffers, and mediators.

3. The reagent kit of claim 1, wherein $R^1$ and $R^2$ are a $C_1$-$C_2$ alkyl group substituted with OH.

4. The reagent kit of claim 1, wherein $R^3$ is $NO_2$.

5. The reagent kit of claim 4, wherein n is 1.

6. The reagent kit of claim 1, wherein the compound of formula (I) is

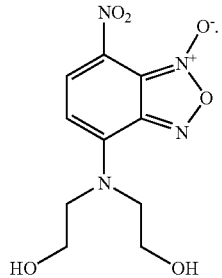

7. The reagent kit of claim 1, wherein the redox indicator is oxidized or reduced by directly accepting an electron from the reducible or oxidizable analyte.

8. A reagent kit that detects an analyte by a redox reaction and a fluorimetric determination, the reagent kit comprising:
 (a) one or more enzymes that reduce or oxidize the reducible or oxidizable analyte; and
 (b) a redox indicator that is oxidized or reduced in the presence of
  (i) the reducible or oxidizable analyte, and
  (ii) the one or more enzymes,
 the redox indicator being a compound of formula (I):

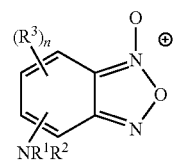

(I)

where $R^1$ and $R^2$ are each independently selected from R, $(CH_2CH_2O)_mR$, COR, COOR, and OCOR;

each $R^3$ is independently selected from $NO_2$, CN, R, OR, OCOR, COOR, SR, and halogen;

R is H or $C_1$-$C_4$ alkyl, where alkyl is optionally substituted with one or more functional group independently selected from the group consisting of halogen, OR, SR, $NR_2$, COOR, $CONR_2$, $SO_3R$ and salts thereof, and $PO(OR)_3$ and salts thereof;

m is an integer from 1 to 20; and n is 1, 2, or 3, wherein, the reducible or oxidizable analyte is selected from the group consisting of glucose, lactate, alcohol, galactose, cholesterol, fructose, glycerol, pyruvate, creatinine, alanine, phenyalanine, leucine, triglycerides, HDL-cholesterol, glutamate-oxalacetate transaminase, glutamate-pyruvate transaminase, alanine aminotransferase, lactate dehydrogenase, and creatine kinase wherein the reducible or oxidzable analyte is glucose and the one or more enzymes is selected from the group consisting of glucose oxidase, glucose dye oxidoreductase, and glucose dehydrogenase/diaphorase.

9. The reagent kit of claim 8, wherein the redox indicator is oxidized or reduced by directly accepting an electron from the reducible or oxidizable analyte.

10. The reagent kit of claim 8, wherein the redox indicator is oxidized or reduced by accepting an electron, directly or via a mediator, from the reducible or oxidizable analyte.

11. The reagent kit of claim 8, wherein the redox indicator is oxidized or reduced by directly accepting an electron from the reducible or oxidizable analyte.

12. The reagent kit of claim 8, wherein $R^1$ and $R^2$ are a $C_1$-$C_2$ alkyl group substituted with OH.

13. The reagent kit of claim 8, wherein $R^3$ is $NO_2$.

14. The reagent kit of claim 13, wherein n is 1.

15. The reagent kit of claim 8, wherein the compound of formula (I) is

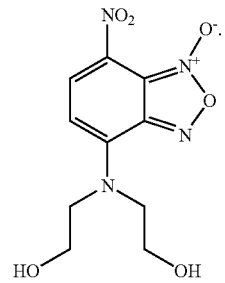

* * * * *

UNITED STATES PATENT AND TRADEMARK OFFICE
CERTIFICATE OF CORRECTION

PATENT NO. : 8,431,410 B2
APPLICATION NO. : 12/757372
DATED : April 30, 2013
INVENTOR(S) : Carina Horn et al.

Page 1 of 1

It is certified that error appears in the above-identified patent and that said Letters Patent is hereby corrected as shown below:

In the Claims

Col. 6, Claim 8, Line 19, "oxidzable" should read --oxidizable--.

Signed and Sealed this
Fifth Day of November, 2013

Teresa Stanek Rea
*Deputy Director of the United States Patent and Trademark Office*